(12) United States Patent
Waizenegger

(10) Patent No.: US 10,932,832 B2
(45) Date of Patent: Mar. 2, 2021

(54) ORTHOGNATHIC SAW AND POSITIONING IMPLANT

(71) Applicant: Karl Leibinger Medizintechnik GmbH & Co. KG, Muehlheim (DE)

(72) Inventor: Axel Waizenegger, Muehlheim (DE)

(73) Assignee: Karl Leibinger Medizintechnik GmbH & Co. KG, Muehlheim (DE)

( * ) Notice: Subject to any disclaimer, the term of this patent is extended or adjusted under 35 U.S.C. 154(b) by 313 days.

(21) Appl. No.: 15/573,327

(22) PCT Filed: Mar. 9, 2016

(86) PCT No.: PCT/EP2016/054988
§ 371 (c)(1),
(2) Date: Nov. 10, 2017

(87) PCT Pub. No.: WO2016/180557
PCT Pub. Date: Nov. 17, 2016

(65) Prior Publication Data
US 2018/0103965 A1  Apr. 19, 2018

(30) Foreign Application Priority Data

May 12, 2015  (DE) ..................... 10 2015 107 484.2

(51) Int. Cl.
*A61B 17/17* (2006.01)
*A61B 17/80* (2006.01)
(Continued)

(52) U.S. Cl.
CPC ........ *A61B 17/8071* (2013.01); *A61B 17/176* (2013.01); *A61B 17/1728* (2013.01);
(Continued)

(58) Field of Classification Search
CPC ..................... A61B 17/176; A61B 17/8071
See application file for complete search history.

(56) References Cited

U.S. PATENT DOCUMENTS

| 5,690,631 | A | 11/1997 | Duncan et al. |
| 5,716,361 | A * | 2/1998 | Masini ................. A61B 17/154 |
| | | | 606/82 |

(Continued)

FOREIGN PATENT DOCUMENTS

| CN | 101360461 A | 2/2009 |
| CN | 102858257 A | 1/2013 |

(Continued)

*Primary Examiner* — Anu Ramana
(74) *Attorney, Agent, or Firm* — Norris McLaughlin, P.A.

(57) ABSTRACT

A bone fusion implant for fusing a first bone region to a second bone region of a mammalian bone includes a first fixing region having multiple securing means receiving holes for attaching to the first bone and a second fixing region which is connected to the first fixing region and has multiple securing means receiving holes for attaching to the second bone region, wherein a cutting tool guiding contour which specifies a severing line is formed between the first and the second fixing region. A method for the individualized production of such a bone fusion implant includes recording an actual 3D model of the mammalian bone implant in a first data set, drafting a target 3D model, and producing the bone fusion implant by way of the target 3D model.

5 Claims, 6 Drawing Sheets

(51) Int. Cl.
    *A61B 34/10*     (2016.01)
    *A61B 17/00*     (2006.01)
    *A61B 17/56*     (2006.01)

(52) U.S. Cl.
    CPC .... *A61B 34/10* (2016.02); *A61B 2017/00004* (2013.01); *A61B 2017/568* (2013.01); *A61B 2034/104* (2016.02); *A61B 2034/108* (2016.02)

(56) References Cited

U.S. PATENT DOCUMENTS

| | | | |
|---|---|---|---|
| 6,960,211 B1 * | 11/2005 | Pfefferle | A61B 17/8085 606/280 |
| 8,088,151 B2 | 1/2012 | Ralph et al. | |
| 9,066,733 B2 * | 6/2015 | Furrer | A61B 17/8071 |
| 9,277,948 B2 * | 3/2016 | Furrer | A61B 17/151 |
| 9,339,279 B2 * | 5/2016 | Dubois | A61B 34/10 |
| 2005/0182408 A1 | 8/2005 | Pfefferle et al. | |
| 2007/0276383 A1 | 11/2007 | Rayhack | |
| 2011/0269100 A1 | 11/2011 | Furrer et al. | |
| 2011/0306976 A1 | 12/2011 | Kubiak et al. | |
| 2012/0022604 A1 | 1/2012 | Polley et al. | |
| 2016/0331427 A1 | 11/2016 | Waizenegger | |
| 2017/0296242 A9 | 10/2017 | Waizenegger | |
| 2018/0103965 A1 | 4/2018 | Waizenegger | |

FOREIGN PATENT DOCUMENTS

| | | |
|---|---|---|
| DE | 299 09 025 U1 | 12/1999 |
| EP | 2 698 122 A1 | 2/2014 |
| EP | 3294168 A1 | 3/2018 |
| RU | 2 259 175 C1 | 8/2005 |
| WO | 2011/136775 A1 | 11/2011 |
| WO | 2011/136898 A1 | 11/2011 |
| WO | 2013/156545 A1 | 10/2013 |
| WO | 2014/043370 A1 | 3/2014 |
| WO | 2014/090964 A2 | 6/2014 |
| WO | 2016/180557 A1 | 11/2016 |

* cited by examiner

ORTHOGNATHIC SAW AND POSITIONING IMPLANT

BACKGROUND OF THE INVENTION

The invention relates to an orthognathic bone fusion implant (also referred to as positioning implant) for an osteotomy application/for fusing a first bone region to a second bone region or plural bone regions of a mammalian bone/bone of a mammal, comprising a first fixing region which has multiple securing means receiving holes and which is provided for attaching to the first bone region and comprising a second fixing region which is connected to the first fixing region, wherein the second fixing region in turn has multiple securing means receiving holes and is provided for attaching to the second bone region. Especially when the mandible, for example, is two-parts, for example in the case of mandibular crowded teeth, there are plural bone regions to which the first bone region is fused. By a mammalian bone/a bone of a mammal an especially hard skeletogenous septum of a vertebrate is understood, hence such a structure of bone tissue. In particular those bones such as fibula and tibia but also cranial bones are also comprised.

From the state of the art, generic bone fusion implants are known already. In this context, for example WO 2014/090964 A2 discloses an implant as well as a guide along with methods for configuring the same. The implant as well as the guide are provided for osteotomy applications on a patient's maxilla and can be designed as a kit. The three-dimensional models of pre-operative and post-operative anatomy are used to define the fixing regions for the guide as well as the implant. Said fixing regions then are further used for defining the structure of the implant as well as the guide. Further state of the art is known from EP 2 698 122 A1, WO 2011/136898 A1, WO 2013/156545 A1 and US 2007/0276383 A1.

Both document WO 2013/156545 A1 and document US 2007/0276383 A1 show different implants of which one implant is inserted prior to performing an osteotomy and an implant different therefrom is used for fusing the bone regions separated from each other.

These configurations known from prior art usually have the drawback, however, that for a cutting processing of the respective mammalian bone to be corrected and subsequently to be fused again, for example a maxilla or mandible, two separate elements have to be used. The severing of the mammalian bone, preferably by means of a sawing process, is realized by a template-type tool guide and the fusion of the two bone regions separated before in the desired position is realized by means of an implant. Thus, it has always been necessary for osteotomy applications so far to produce both a user-defined tool guide and a user-defined positioning implant. This required a relative expensive manufacture of the elements used for the osteotomy applications and consequently indirectly also relatively high operating costs.

BRIEF SUMMARY OF THE INVENTION

Therefore, it is the object of the present invention to eliminate said drawbacks known from the state of the art and, especially, to provide a bone fusion implant which further reduces the expenditure of an osteotomy treatment, while at the same time patient-specific/individualized adaptation of the bone fusion implant is to be guaranteed.

This object is achieved, according to the invention, by the fact that between the first and second fixing regions a (first) cutting tool guiding contour specifying a (first) severing line is formed. By a position between the first and second fixing regions the (spatial) position is designated which is located, when viewed in a spatial extension along the mammalian bone, between the first fixing region and the second fixing region. The cutting tool guiding contour is thus arranged between a side of the first fixing region facing the second fixing region and a side of the second fixing region facing the first fixing region.

Such configuration enables the bone fusion implant to be used not only as a positioning implant but also for the preceding severing of the two bone regions of the mammalian bone as a severing template. Thus, the correction of the respective malformation of the mammalian bone is implemented in an especially cost-efficient manner. Another advantage to be mentioned using the same implant for severing and re-fusing especially also resides in the fact that manufacturing tolerances between the previously separately configured tool guide and the positioning implant are avoided. The two bone regions then are arranged after fusion definitely more precisely in the afore-calculated target position so that the healing process of the mammalian bone is further promoted.

It is furthermore advantageous when the (first) cutting tool guiding contour is strip-shaped. In this way, the cutting tool, for example a saw/circular saw, is backed by the cutting tool guiding contour in an especially stable manner so as to sever the two bone regions along the severing line/osteotomy line.

In addition, it is of advantage when the cutting tool guiding contour is configured directly by a connecting bar connected to the first fixing region and/or the second fixing region. This allows for an especially compact design of the bone fusion implant.

When the cutting tool guiding contour is formed by an inner edge of a frame structure designed/configured between the first fixing region and the second fixing region, it is intended that the cutting tool guiding contour is arranged on an especially dimensionally stable region of the bone fusion implant and the structure thereof cannot be simply modified by the severing operation.

When the (first and second) fixing regions and the cutting tool guiding contour are formed/fused in one material/integrally with each other, the bone fusion implant is even more stable. Accordingly, further preferably the fixing regions and the cutting tool guiding contour are configured to be dimensionally stable relative to each other.

It is also of advantage when the bone fusion implant is manufactured/completely made from a bio-compatible and/or bio-absorbable material. This renders the bone fusion implant usable in an especially efficient manner.

In this context, it is also particularly advantageous when the bone fusion implant is made from a metal material, preferably a titanium material. Of further preference, the titanium material is heat-treated. Thus, a bone fusion implant which in itself is especially dimensionally stable is realized.

Also, it is useful when between the second fixing region and a further third fixing region another/second cutting tool guiding contour specifying a (second) severing line is formed, wherein the third fixing region in turn includes multiple securing means receiving holes and is prepared for attaching to the first bone region. In this way, the two bone regions are even more stably secured in position relative to each other in a condition fixed by both bone regions. The second cutting tool guiding contour is configured, of further preference, like the first cutting tool guiding contour.

It is also advantageous when the bone fusion implant is provided for fusing a first bone region to a second bone region of an upper jaw bone/a maxilla or a lower jaw bone/a mandible. This renders the bone fusion implant to work especially efficiently.

In addition, the invention also relates to a method for the individualized manufacture of the bone implant according to at least one of the afore-described embodiments, comprising the following steps preferably being carried out successively in time:
a) recording an actual 3D model of the mammalian bone to be treated in a first data set;
b) creating a target 3D model in a second data set by fixing at least one severing line on the actual 3D model as well as by moving two imaginary bone regions relative to each other (i.e. the first bone region relative to the second bone region), and
c) manufacturing the bone fusion implant by way of the target 3D model/the second data set, wherein the first fixing region is formed for fixing to the first (imaginary) bone region of the target 3D model, the second fixing region is formed for fixing to the second (imaginary) bone region of the target 3D model and the cutting tool guiding contour is formed by at least partially emulating the severing line.

In this way, especially efficient production of a bone fusion implant is realized.

Moreover, the invention also relates to a method for treating a preferably human mammalian bone making use of a bone fusion implant according to any one of the afore-mentioned embodiments, comprising the following steps of:
a) attaching the bone fusion implant with a first fixing region to a first bone region of the mammalian bone,
b) severing the mammalian bone along a severing line while a cutting tool contacts the cutting tool guiding contour,
c) aligning the second bone region severed from the first bone region in the desired target position, and
d) securing the second fixing region to the second bone region.

In this way, also a treatment process is configured especially efficiently.

BRIEF DESCRIPTION OF THE DRAWINGS

Hereinafter the invention shall be illustrated in detail by way of Figures, wherein.

DETAILED DESCRIPTION OF THE INVENTION

Figure 1:
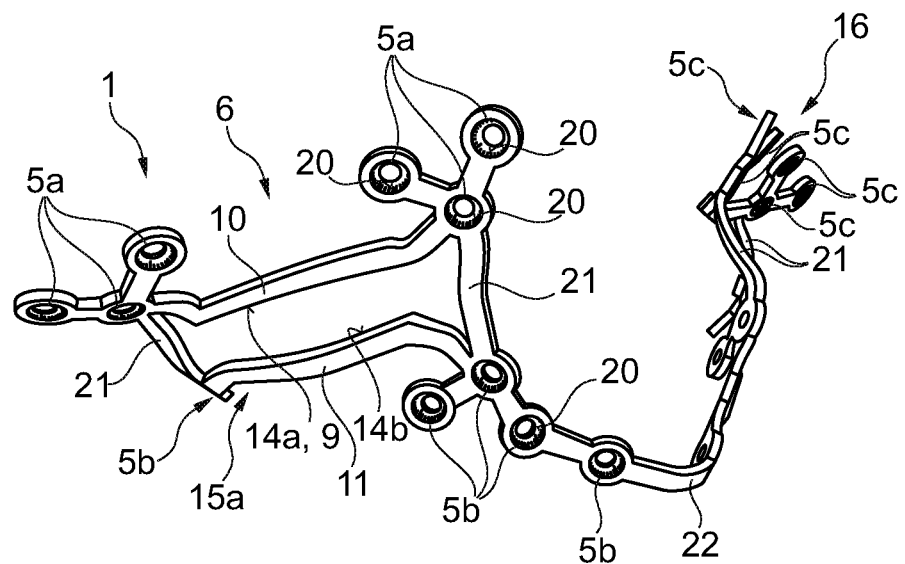
FIG. 1 shows an isometric representation of a bone fusion implant according to the invention in accordance with an advantageous embodiment, wherein first and second fixing regions as well as a (first) cutting tool guiding contour formed on a connecting bar of the first fixing region is especially clearly evident.

The Figures are merely schematic and serve exclusively for the comprehension of the invention. Like elements are provided with like reference numerals.

From FIG. 1 a bone fusion implant 1 according to the invention in accordance with a preferred embodiment is especially clearly evident. In this figure, especially a first fixing region 6 which has multiple securing means receiving holes 5a and is provided for attaching to a first bone region 2 of a mammalian bone 4 as well as a second fixing region 7 which is connected to the first fixing region 6 is evident. Also, the second fixing region 7 again includes multiple securing means receiving holes, hereinafter referred to as second securing means receiving holes 5b, thus allowing the second fixing region 7 to be provided for attaching to a second bone region 3 of the mammalian bone 4.

Figure 2:
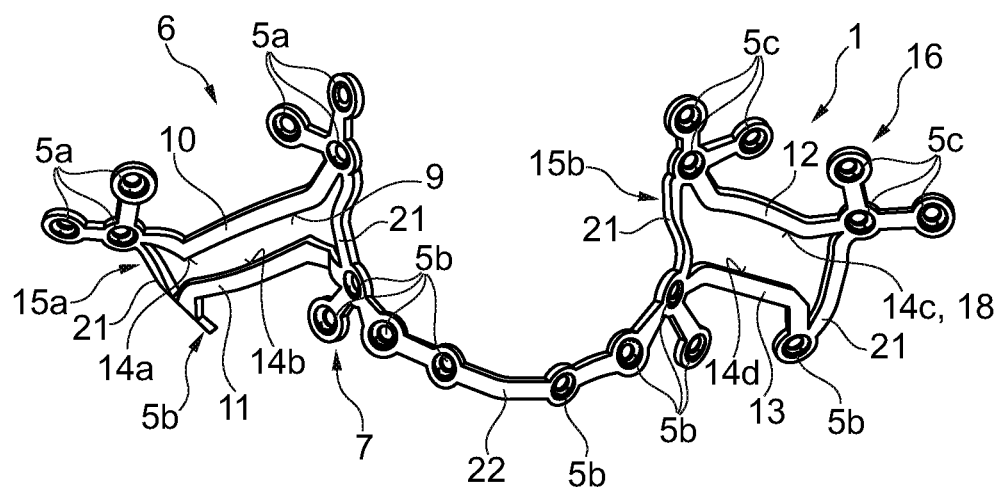
FIG. 2 shows a front view of the bone fusion implant shown in FIG. 1, wherein in this case, apart from the first and second fixing regions, a further third fixing region equally connected to the second fixing region is evident, said third fixing region in turn including a connecting bar forming a (second) cutting tool guiding contour.

As it is then further clearly visible from FIG. 2, the second fixing region 7 which is substantially formed by means of a main bar 22 is also fused to a third fixing region 16. On the main bar 22 the second securing means receiving holes 5b are juxtaposed in a chain-type manner. The main bar 22 in turn forms second and third connecting bars 11, 13, as will be described in detail below. The third fixing region 16 again is configured substantially like the first fixing region 6 and equally has plural securing means receiving holes hereinafter referred to as third securing means receiving holes 5c. Said third securing means receiving holes 5c again serve for securing to the first bone region 2, as will be illustrated in detail in the following. Each of the first fixing region 6 and the third fixing region 16 has two groups of first and, resp., third securing means receiving holes 5a, 5c arranged in triangular shape relative to each other.

The first securing means receiving holes 5a are arranged on a first connecting bar 10 assigned to the first fixing region 6 which connecting bar is aligned substantially horizontally in a condition secured to the mammalian bone 4. Thus, the first fixing region 6 forms the first connecting bar 10 which is strip-shaped and interconnects the two groups of the first securing means receiving holes 5*a* (each including three first securing means receiving holes 5*a*). Then to the first fixing region 6 in turn two bridging bars 21 aligned substantially perpendicularly to the first connecting bar 10 are connected. Each of the bridging bars 21 is formed integrally with the first fixing region 6 in the area of a securing means receiving hole 5*a*. The bridging bars 21 connect the first fixing region 6 and, resp., the first connecting bar 10 to the equally strip-shaped second connecting bar 11 formed on the second fixing region 7 and extending substantially in parallel to the first connecting bar 10. The two bridging bars 21 as well as the second connecting bar 11 of the second fixing region 7 form, together with the first connecting bar 10 of the first fixing region 6, a first substantially diamond-shaped/rectangular frame structure 15*a*.

In the same way, the third fixing region 16 is then connected to the second fixing region 7. The third securing means receiving holes 5*c* are arranged on a third connecting bar 12 assigned to the third fixing region 16 which in a condition secured to the mammalian bone 4 is substantially horizontally aligned. Thus, the third fixing region 16 constitutes the third connecting bar 12 which is strip-shaped and interconnects the two groups of the third securing means receiving holes 5*c* (each having three third securing means receiving holes 5*c*). Then in turn two bridging bars 21 aligned substantially perpendicularly to the third connecting bar 12 are connected to the third fixing region 16. Each of the bridging bars 21 is integrally formed with the third fixing region 16 in the area of a securing means receiving hole 5*c*. The bridging bars 21 connect the third fixing region 16 and, resp., the third connecting bar 12 to an equally strip-shaped fourth connecting bar 13 formed on the second fixing region 7 which extends substantially in parallel to the third connecting bar 12. The two bridging bars 21 as well as the fourth connecting bar 13 of the second fixing region 7 form, together with the third connecting bar 12 of the third fixing region 16, a second substantially diamond-shaped/rectangular frame structure 15*b*.

In this embodiment, the first frame structure 15*a* is designed somewhat differently from the second frame structure 15*b*. The second frame structure 15*b* is designed differently such that a distance between the third and fourth connecting bars 12, 13 is larger than a distance between the first and second connecting bars 10, 11.

The third securing means receiving holes 5*c* in turn are designed equal to the first and second securing means receiving holes 5*a*, 5*b*. All of the securing means receiving holes 5*a*, 5*b*, 5*c* form seats for securing means in the form of bone screws in a usual manner, wherein each of the securing means receiving holes 5*a*, 5*b*, 5*c* includes a conical screw head contact face 20 on a side facing away from the respective bone region 2, 3. In the secured state of the bone fusion implant 1 to the two bone regions 2, 3 the screw heads of the bone screws then are completely countersunk in said securing means receiving holes 5*a*, 5*b*, 5*c*.

As is furthermore clearly visible from a synopsis of FIGS. 1 and 2, both the fixing regions 6, 7, 16 and a respective cutting tool guiding contour 9, 18 arranged on the respective frame structure 15*a*, 15*b* are formed integrally, i.e. from one piece of material, with each other.

In this configuration, an inner edge, viz. the first inner edge 14*a* of the first connecting bar 10, directly form a first cutting tool guiding contour 9 which is provided to serve as a guide rail for a cutting tool, i.e. a saw tool/a circular saw.

The first cutting tool guiding contour 9 emulates a first severing line 8 to be produced in the mammalian bone 4. As an alternative or in addition to this, it is also possible to configure the (second) inner edge 14*b* of the second connecting bar 11 as such first cutting tool guiding contour 9. The first and second inner edges 14*a*, 14*b* are those side edges of the connecting bars 10, 11 which are facing each other.

Moreover, also the (third) inner edge 14*c* of the third connecting bar 12 is configured as a cutting tool guiding contour, viz. as second cutting tool guiding contour 18. The second cutting tool guiding contour 18, too, serves as guide rail for a cutting tool, viz. a saw tool/circular saw for severing the first bone region 2 from the second bone region 3. The second cutting tool guiding contour 18 emulates a second severing line 17 to be produced in the mammalian bone 4. As an alternative or in addition to this, it is also possible to provide again the (fourth) inner edge 14*d* of the fourth connecting bar 13 as such second cutting tool guiding contour 18. The third and fourth inner edges 14*c*, 14*d* are those side edges of the connecting bars 10, 11 which are facing each other.

The second and fourth connecting bars 10, 11 also are an integral part of the main bar 22 which interconnects the two frame structures 15*a*, 15*b* arranged in wing shape in a dimensionally stable manner. It is also referred to the fact that according to a further embodiment it is realized that the main bar 22 is configured centrally between the frame structures 15*a*, 15*b* with a reclosable mechanism, whereupon the frame structures 15*a*, 15*b* can be secured to the bone regions 2, 3 independently of each other and, subsequently, can be interconnected via the mechanism again in a dimensionally stable manner.

The bone fusion implant 1 is formed/produced, due to its configuration as an implant, of biocompatible material, viz. a hardened titanium material. The bone fusion implant 1 in addition or as an alternative thereto may also be partly or completely produced of bio-absorbable material/to be bio-absorbable.

In connection with FIGS. 3 to 9, also a method for producing a bone implant 1 according to the invention is especially clearly evident. For this purpose, as is evident from FIG. 3 for example, at first an actual 3D model of the mammalian bone 4 in the form of a human cranium here and to be treated by means of osteotomy is created. This is done by means of a tomographic image detection device (CT method) scanning the mammalian bone 4 and establishing a first data set which contains/reflects the three-dimensional shape of the mammalian bone 4.

Said mammalian bone 4 already includes a malformation of a maxilla/an upper jaw bone 19 of the mammalian bone 4 which can be remedied by a severing dysgnathic surgery/an osteotomy treatment. By way of said imaginary actual 3D model then a target 3D model of the maxilla/the mammalian bone 4 is produced, wherein for each first and third fixing region 6, 16 a severing line 8 and, resp., 17 is determined on the imaginary actual 3D model. To each of the severing lines 8, 17 being arranged on the actual 3D model one of the cutting tool guiding contours 9, 18 is assigned and, resp., one of the cutting tool guiding contours 9, 18 is formed corresponding to said severing lines 8, 17. After specifying said two severing lines 8, 17, the two bone regions 2, 3 are fictitiously separated from each other and are moved relative to each other to the desired relative position so that finally an imaginary target 3D model (calculated in a second data set) is resulting in FIG. 9, according to which the fixing regions 6, 7, 16 are adapted to the shape of said target 3D model. The fixing regions 6, 7, 16 are adapted to each other and deformed so that the first and third fixing regions 6, 16 are adapted for full-surface contact with the first bone region 2 and the second fixing region 7 is adapted for full-surface contact with the second bone region 3.

Figure 3:
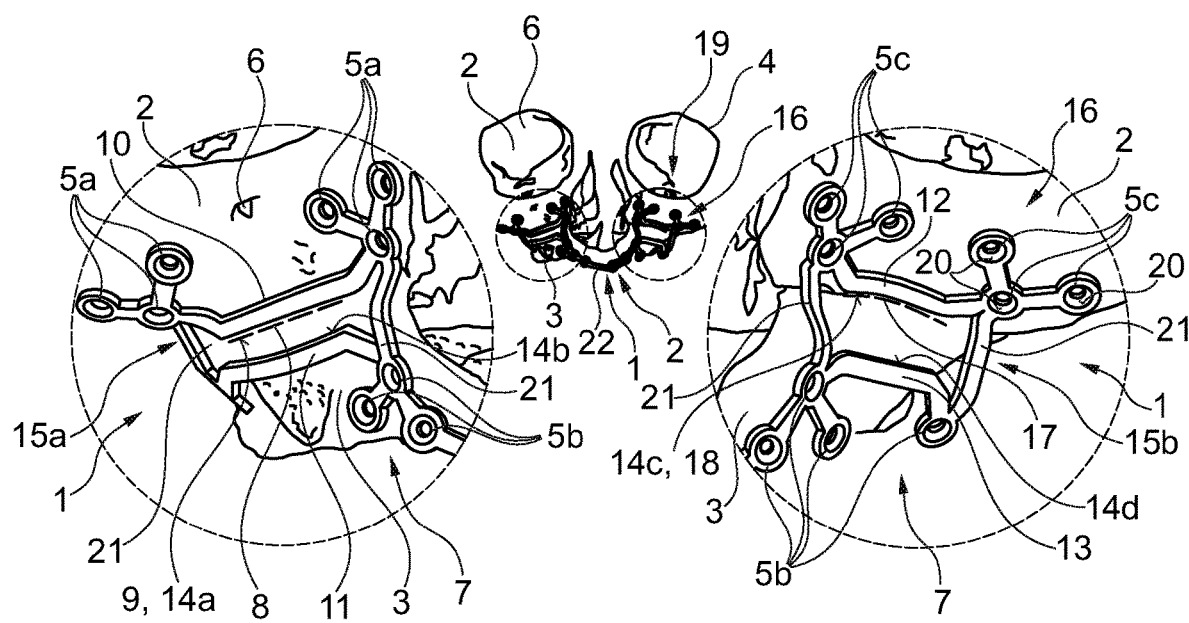
FIG. 3 shows a front view of an actual 3D model of a mammalian bone in the form of a human cranium, wherein, according to the two secondary detailed views, each of the first and the third fixing region of the bone fusion implant according to FIGS. 1 and 2 is secured to a maxilla of the cranium and the severing lines are optically emphasized at the cutting tool guiding contours.
Figure 4:
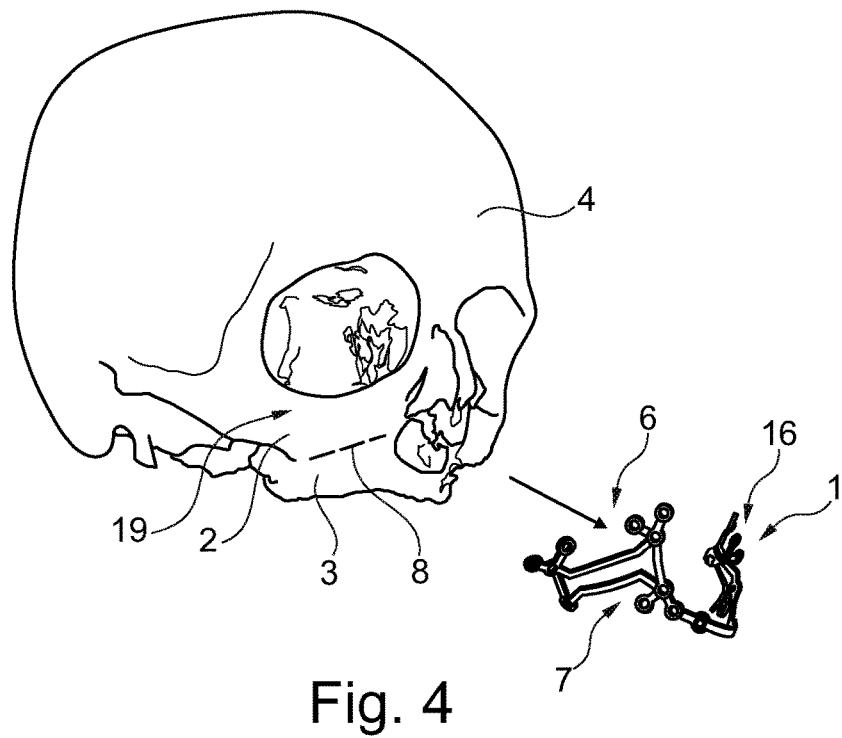
FIG. 4 shows an isometric representation of the actual 3D model shown in FIG. 3 after implementing a partial cut in the maxilla formed by means of a cutting tool along the cutting tool guiding contours as well as after subsequently removing the bone fusion implant from the actual 3D model.
Figure 5:
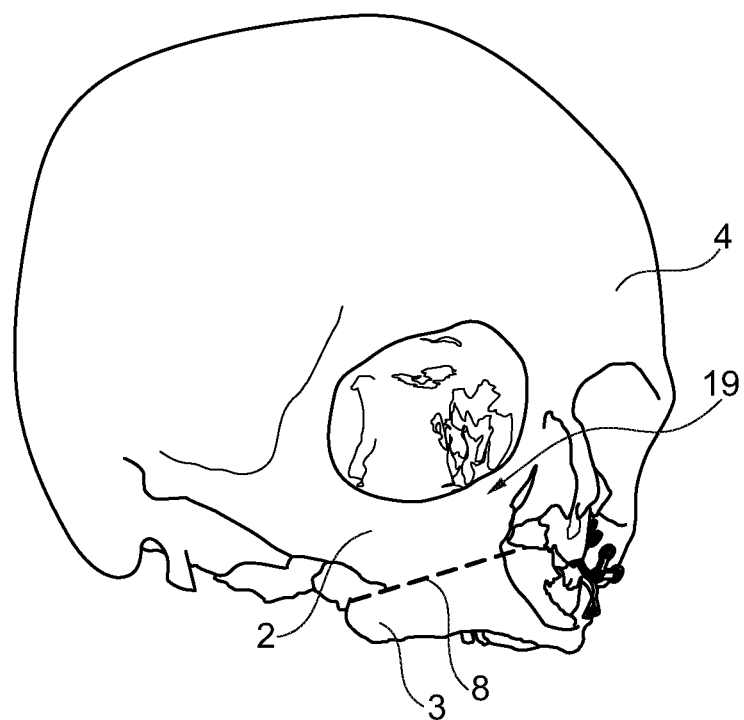
FIG. 5 shows an isometric representation of the actual 3D model after implementing a complete severing of the maxilla along the severing lines partially formed before, one severing line being optically emphasized.
Figure 6:
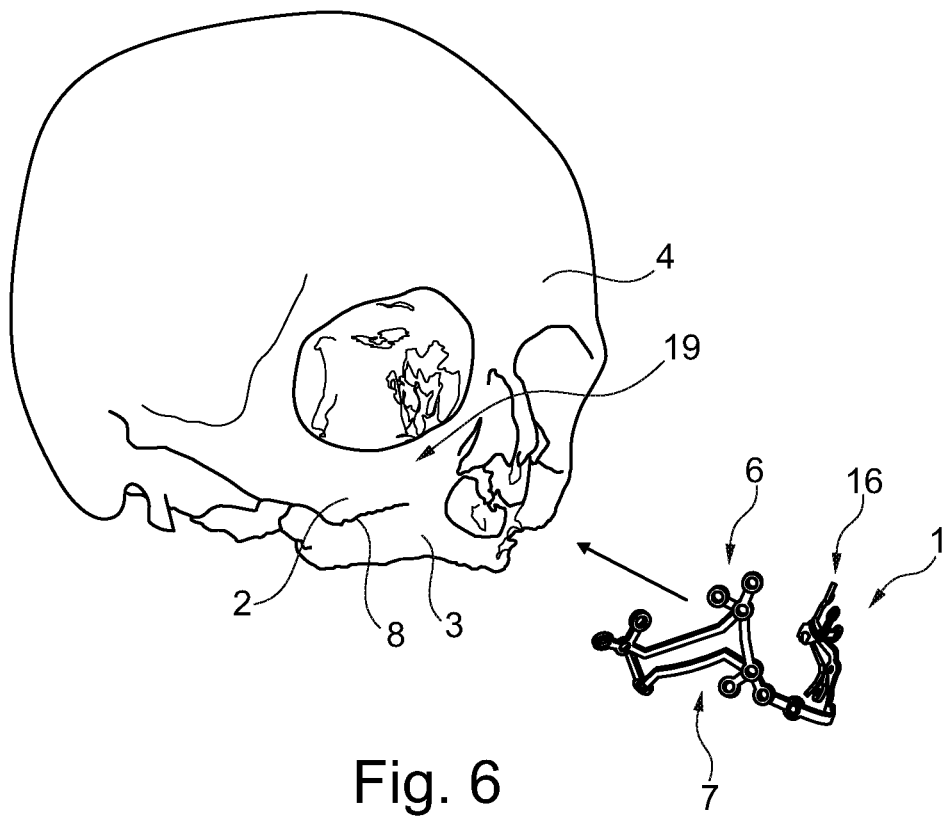
FIG. 6 shows an isometric representation of the actual 3D model with the two previously severed bone regions of the maxilla before the bone fusion implant is fixed again.
Figure 7:
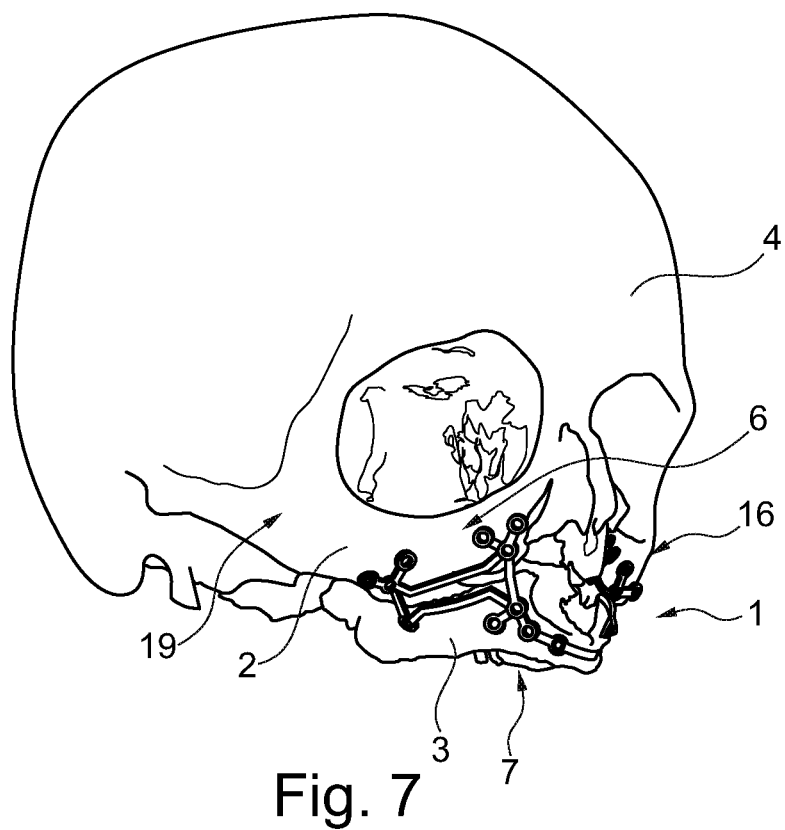
FIG. 7 shows an isometric representation of the actual 3D model in a re-attached state of the bone fusion implant in which the first and third fixing regions are in turn attached to the first bone region, but the second fixing region is still spaced apart from the second bone region.
Figure 8:
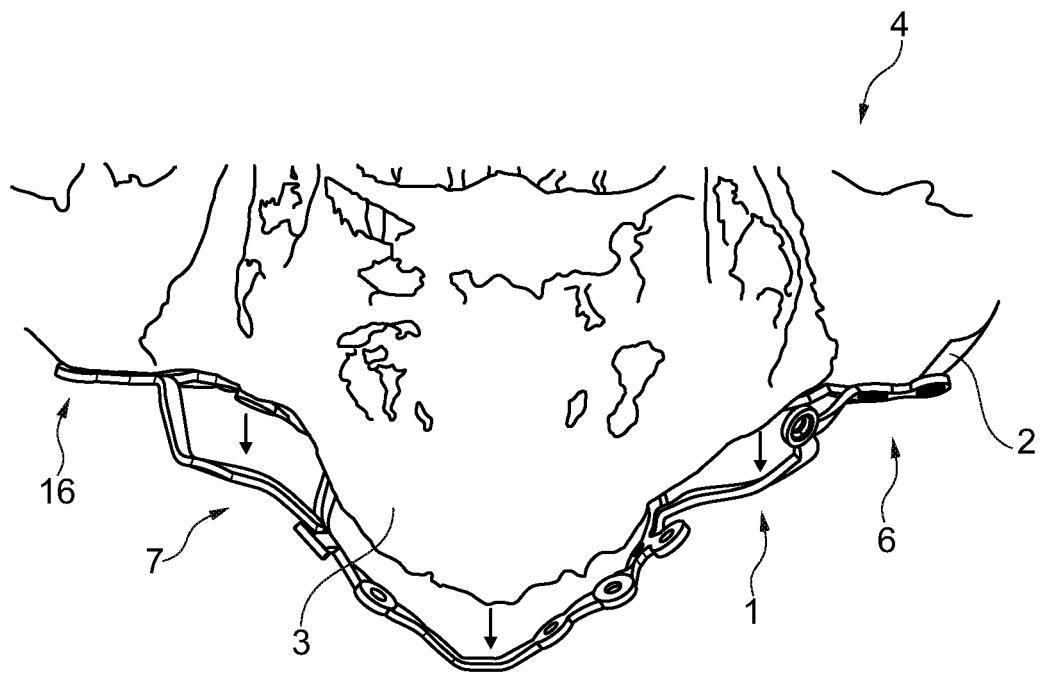
FIG. 8 shows a bottom view of the actual 3D model in which the cranium is shown from a lower side in which the second bone region is moved relative to the first bone region along the shifting arrows until the second bone region contacts the second fixing region.
Figure 9:
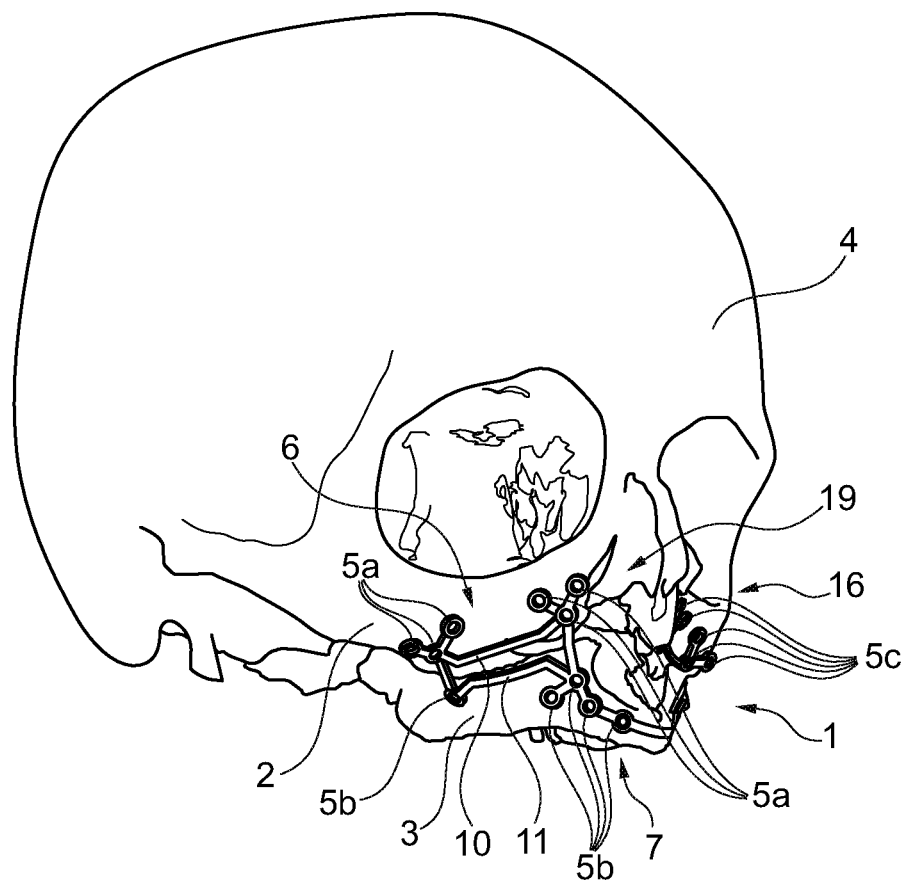
FIG. 9 shows an isometric representation of the actual 3D model with a completely attached bone fusion implant which is tightly fused to the first bone region and, resp., the second bone region both in the first and third fixing regions and in the second fixing region.

Also, in connection with FIGS. 3 to 9 a treatment process of the mammalian bone 4/cranium is especially clearly evident. For this purpose, initially the already produced bone fusion implant 1 is secured to the mammalian bone 4 by means of the first and third fixing regions 6, 16, whereas the second fixing region 7 still remains separated from the second bone region 3 of the maxilla (FIG. 3). Subsequently, along the severing lines 8, 17 formed by the cutting tool guiding contours 9 and 18 the two bone regions 2, 3 are partially severed from each other within the frame structures 15a and 15b, which is visible from the secondary detailed views in FIG. 1. Subsequently, according to FIG. 4 the bone fusion implant 1 then is detached and removed from the first bone region 2 and, in the step according to FIG. 5, the first bone region 2 is completely severed from the second bone region 3 by further sawing along the already drafted severing line 8, 17. After the two bone regions 2 and 3 have been completely separated from each other, the bone fusion implant 1 is again secured with the first and the third fixing region 6, 16 to the first bone region 2 (FIG. 6), wherein in each securing means receiving hole 5a, 5c a bone screw is introduced which in turn is screwed into the first bone region 2. In a secured condition of the two fixing regions 6 and 16 to the first bone region 2 according to FIG. 7, then, in accordance with FIG. 8, the second bone region 3 detached from the first bone region is moved relative to the first bone region 2 until, according to FIG. 9, the second bone region 3 contacts the second fixing region 7 especially in the area of the second securing means receiving holes 5b. In this intended corrected position between the first and the second bone region 2, 3, then in turn plural bone screws are introduced to the second securing means receiving holes 5b and are screwed with the second bone region 3. Finally, this results in the fact that the two bone regions 2, 3 are tightly fused to each other by the bone fusion implant 1.

In other words, the idea according to the invention thus resides in the combination of a sawing template and a patient-specific orthognathic implant forming a combined saw and positioning implant 1. It is of particular advantage that required positioning aids such as e.g. splints, navigation instruments, marking screws and milling lines can be omitted. Also, the additional drilling template then is omitted. In addition, the precision of planning implementation and operative intervention is improved, wherein also the germinal load is improved by the omission of an additional potential carrier. The course of operation is also facilitated by the reduction of the individual operating steps. In addition, the operating time is reduced by the omission of additional instrument changes and said reduction of the individual steps. In this way, finally also a more cost-efficient production is realized by reducing the production steps.

In the configuration of the bone fusion implant 1 according to the invention, for each side two horizontally extending bars 10, 11; 12, 13 are located in the area of the right and left maxillary walls extending from the crista zygomaticoalveolaris to the respective lateral side of the foramen piriformis. Each of said two bars 10, 11; 12, 13 forms a guide corresponding to a sawing template by the interstice/slit formed. The interstice may also extend non-parallel when a bony resection is to be carried out. In this case, the lower edge 14a; 14c of the upper bar and the upper edge of the lower bar 14b; 14d serves as a guide for osteotomy. When required, the bars 10, 11; 12, 13 can be provided with boreholes so as to obtain further fixing options. The horizontally directed bars 10, 11; 12, 13 are connected to four vertically directed bars 21 which constitutes a bond between the upper and the lower pair of bars 10, 11; 12, 13. The planned displacing information is encoded by bends in this region. The two horizontally directed bars 10, 11; 12, 13 on the right and on the left are connected to a respective vertical bar 21 in the outer region (laterally) so as to achieve sufficient stability in this region. They may be extended, when required, in the direction of the zygomatic bone so as to obtain additional fixing options by osteosynthesis screws (bone screws). Paranasal on both sides there are located vertically directed bars including boreholes for further fixation. A horizontally directed bar 10, 11; 12, 13 connects the right and left sides below the nasal spine. In the area of the nasal spine the connection can also be made in situ by an anchoring or lock principle during operation so that upon initial insertion a large implant can be disintegrated into individual parts. Plural jaw parts, such as e.g. the tripartite Le Fort I osteotomy, can equally be provided with said type of implant.

Figure 10:
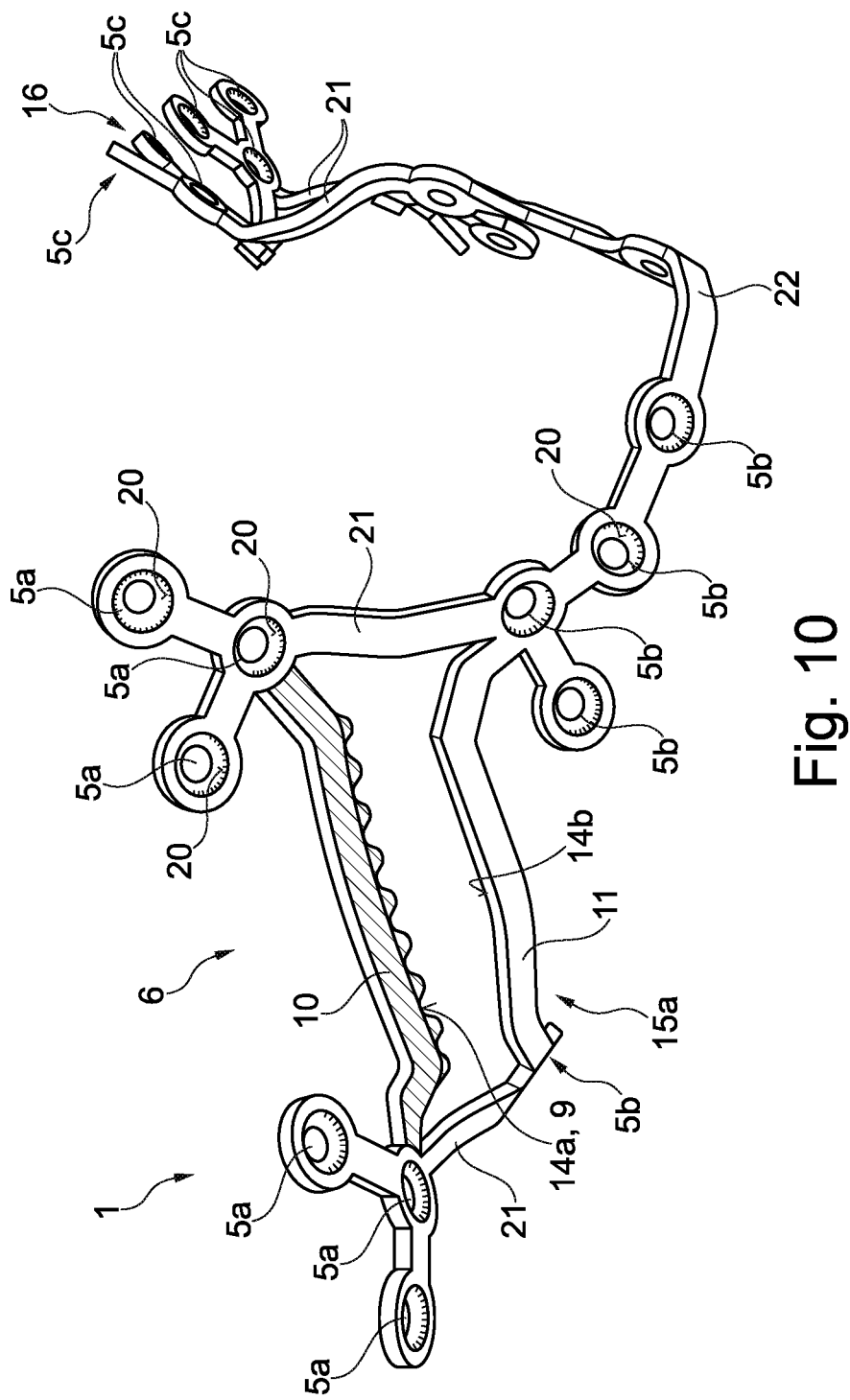
FIG. 10 shows another embodiment in which a lower side of an upper connecting bar is wave-shaped or zigzag-shaped.

Although in FIG. 10 only a wave-shaped lower side of a connecting bar 10 is shown, there may be provided plural of such geometrically alternating structures, especially at all those positions which serve as cutting tool guiding contour 9. This offers the advantage that the contact surface for the tool used for bone severing such as a saw blade is reduced. Moreover, consideration have been made to the effect that it would also be reasonable when the "saw guiding region" could be severed after introducing the saw cut, possibly by pinching off as in the case of a "Revell kit", so as to reduce the material input. Then also the shape could be designed like a guide slit in which e.g. an oscillating knife is guided. The "stop strip" can be formed "wave-shaped" at least on one side, possibly also on two sides, so as to minimize the contact face with the saw blade.

LIST OF REFERENCE NUMERALS 1 bone fusion implant
2 first bone region
3 second bone region
4 mammalian bone
5a first securing means receiving hole
5b second securing means receiving hole
5c third securing means receiving hole
6 first fixing region
7 second fixing region
8 first severing line
9 first cutting tool guiding contour
10 first connecting bar
11 second connecting bar
12 third connecting bar
13 fourth connecting bar
14a first inner edge
14b second inner edge
14c third inner edge
14d fourth inner edge
15a first frame structure
15b second frame structure
16 third fixing region
17 second severing line
18 second cutting tool guiding contour
19 maxilla
20 screw head contact face 21 bridging bar
22 main bar

The invention claimed is:

1. A bone fusion implant configured to guide a cutting tool to sever at least one first bone region of a mammalian bone from at least one second region of the mammalian bone by osteotomy and to fuse the at least one first bone region of the mammalian bone to the at least one second bone region of the mammalian bone severed from the first bone region by the osteotomy, comprising flat bars forming a closed frame and having no holes between ends thereof, the closed frame having a securing means receiving hole at each corner thereof, additional flat bars integral with and extending laterally outwardly from respective corners of the frame and each of the additional flat bars having a free end being provided with a securing means receiving hole proximate the free end, an inner edge of at least one of the flat bars of the closed frame being comprised of a plurality of serially arranged mutually adjacent cutting tool guiding indentations configured to guide a cutting tool along a severing line on the mammalian bone to effect the osteotomy, the severing line separating the first bone region from the second bone region.

2. The bone fusion implant according to claim 1, wherein the bone fusion implant is formed of one piece of material.

3. The bone fusion implant according to claim 1, wherein the bone fusion implant is made from a metal material.

4. The bone fusion implant according to claim 1, wherein the bone fusion implant is configured for fusing a first bone region to a second bone region of a maxilla or a mandible.

5. A method for the individualized production of the bone fusion implant according to claim 4, comprising the following steps of:
   a) recording an actual 3D model of the mammalian bone in a first data set,
   b) drafting a target 3D model in a second data set by determining at least one severing line on the actual 3D model as well as by relatively moving two imaginary bone regions separated by the at least one severing line relative to each other, and
   c) producing the bone fusion implant by way of the target 3D model, wherein a first fixing region of the bone fusion implant is formed for fixing to the first bone region of the target 3D model, a second fixing region of the bone fusion implant is formed for fixing to the second bone region of the target 3D model and the cutting tool guiding contour of the bone fusion implant is formed by at least partially emulating the at least one severing line.

* * * * *